(12) United States Patent
Butsch

(10) Patent No.: US 9,242,351 B2
(45) Date of Patent: Jan. 26, 2016

(54) BIPOLAR FORCEPS

(76) Inventor: Thomas Butsch, Rietheim-Weilheim (DE)

(*) Notice: Subject to any disclaimer, the term of this patent is extended or adjusted under 35 U.S.C. 154(b) by 1228 days.

(21) Appl. No.: 13/171,575

(22) Filed: Jun. 29, 2011

(65) Prior Publication Data

US 2012/0004653 A1 Jan. 5, 2012

(30) Foreign Application Priority Data

Jun. 30, 2010 (DE) .................. 10 2010 025 742

(51) Int. Cl.
| | |
|---|---|
| *A61B 18/18* | (2006.01) |
| *B25B 9/02* | (2006.01) |
| *A61B 17/30* | (2006.01) |
| *A61B 18/14* | (2006.01) |

(52) U.S. Cl.
CPC . *B25B 9/02* (2013.01); *A61B 17/30* (2013.01); *A61B 18/1442* (2013.01); *A61B 2018/1462* (2013.01); *Y10T 29/49117* (2015.01)

(58) Field of Classification Search
CPC ............... A61B 17/30; A61B 18/1442; A61B 2018/1462; B25B 9/02
USPC .................................................... 606/45–52
See application file for complete search history.

(56) References Cited

U.S. PATENT DOCUMENTS

| | | | |
|---|---|---|---|
| 3,685,518 A | | 8/1972 | Beuerle et al. |
| 6,293,946 B1 | * | 9/2001 | Thorne .......................... 606/48 |
| 2006/0276785 A1 | * | 12/2006 | Asahara et al. ................. 606/51 |
| 2007/0265619 A1 | * | 11/2007 | Ariola et al. .................... 606/51 |
| 2008/0200914 A1 | * | 8/2008 | Hanlon et al. .................. 606/48 |

FOREIGN PATENT DOCUMENTS

| | | |
|---|---|---|
| DE | 60027311 | 1/2007 |
| DE | 102008022889 A1 | 6/2009 |
| WO | WO01/15615 | 3/2001 |
| WO | WO2006/103671 | 10/2006 |

* cited by examiner

*Primary Examiner* — Michael Peffley
*Assistant Examiner* — Amanda Zink
(74) *Attorney, Agent, or Firm* — Schroeder & Siegfried, P.A.

(57) ABSTRACT

The limbs of a bipolar forceps for RF coagulation are produced from a bimetal material, wherein an outer layer (18) consists of stainless steel and determines the mechanical properties of the forceps, while an inner layer (20) consists of a sliver alloy. An electrode (30) is formed from the inner layer at the distal end of the limbs (16). The inner layer (20) brings about good heat dissipation from the electrodes (30) and prevents the tissue from sticking thereto during coagulation.

10 Claims, 3 Drawing Sheets

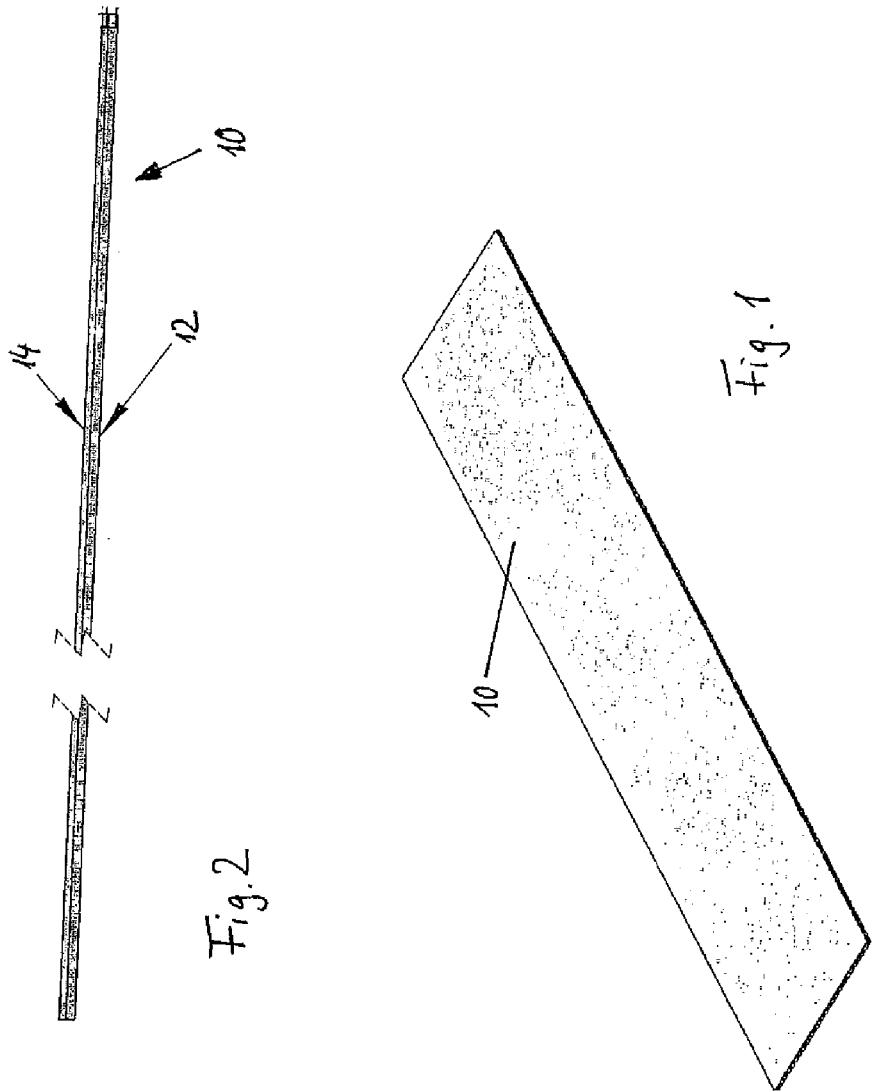

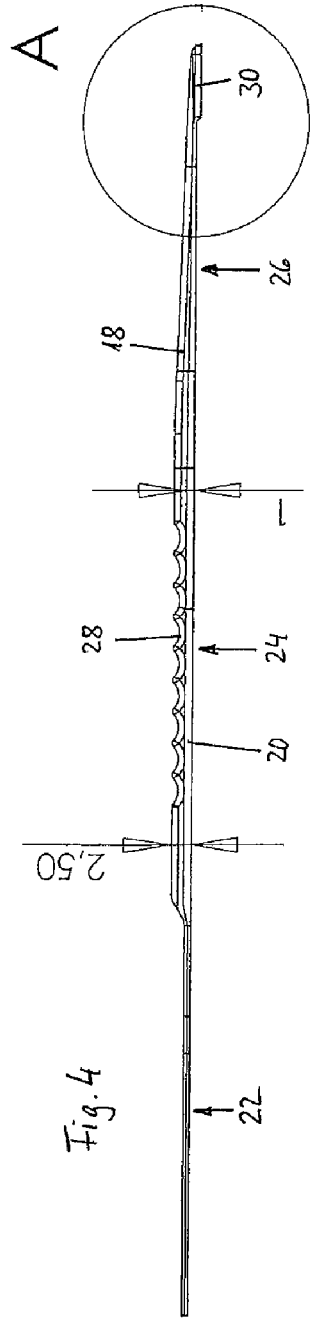
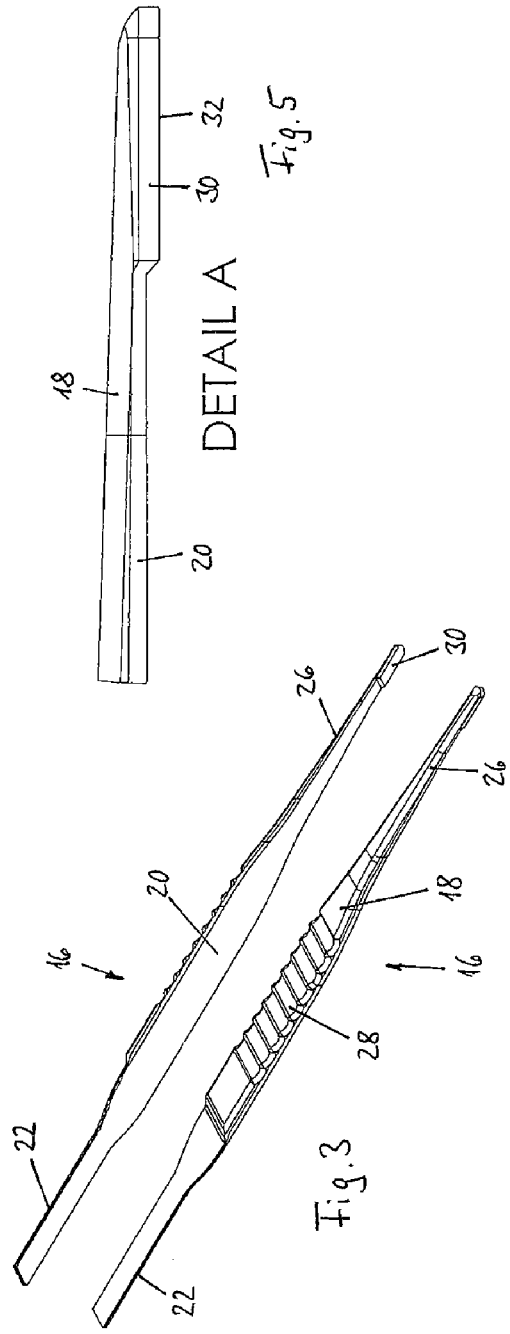

BIPOLAR FORCEPS

BACKGROUND OF THE INVENTION

The invention relates to a bipolar forceps, more particularly for RF coagulation, as per the preamble of patent claim 1.

In surgery, bipolar forceps are used for coagulating the tissue of a patient. To this end, radiofrequency AC current is generally conducted through the tissue in order to heat and coagulate the latter. The forceps used for this purpose have differently shaped limbs, depending on intended use, with respectively one electrode being formed at the distal tips of the two limbs. The tissue to be coagulated is brought between the electrodes. The RF current is supplied via a plug-in connector attached proximally on the forceps and conducted through tissue via the electrodes.

A problem in the case of these bipolar forceps is that the RF current heats not only the tissue situated between the electrodes. The electrical contact resistance between the tissue and the contact areas of the electrodes touching the tissue also leads to heating of the electrodes. The heating of the electrodes can lead to the tissue sticking to the contact area of the electrodes. This leads to dirtying of the contact areas by the stuck-on tissue and increases the contact resistance for subsequent coagulations. Moreover, the tissue sticking-on can lead to stuck-on tissue parts being carried along when the forceps is removed and the tissue being damaged as a result of this.

In order to counteract this sticking-on of the tissue, the heating of the electrodes is known to be reduced by providing the electrodes with a metal, which has a high thermal conductivity for dissipating heat from the contact area of the electrodes. Moreover, this metal must have good electrical conductivity in order to conduct the RF current. Finally, the metal must be biocompatible, i.e. it must not damage the tissue chemically. Suitable metals with these properties are, in particular, the precious metals silver and gold, wherein silver should be preferred, more particularly also for reasons of cost. In the case of a bipolar forceps known from EP 1 210 022 B1, the distal tips of the limbs, consisting of stainless steel, of the forceps are for this purpose surrounded by a layer of silver or gold. This layer forms the electrodes with the contact areas thereof and at the same time forms a heat reservoir with a relatively large heat capacity for absorbing heat dissipated from the contact area. In the case of a bipolar forceps known from DE 10 2008 022 889 A1, a channel leading to the contact area of the electrodes is worked into the distal ends of the limbs, consisting of stainless steel, of the forceps, which channel is filled with silver to form a heat conduction channel for dissipating the heat from the contact areas. In these known bipolar forceps, the formation of the heat dissipation is connected with additional work steps during the production of the forceps.

BRIEF SUMMARY OF THE INVENTION

The invention is based on the object of simplifying the production of a bipolar forceps as per the preamble of claim 1.

According to the invention, this object is achieved by a bipolar forceps with the features of patent claim 1. According to the invention, such a forceps is produced by a method as per patent claim 9.

Advantageous embodiments of the invention are specified in the dependent claims.

In the case of the bipolar forceps according to the invention, the two limbs of the forceps are each produced from a bimetal material, which consists of a first layer of an elastically resilient metal and a second layer made of a metal with high electrical and thermal conductivity. The bimetal material is produced in a fashion known per se by placing a strip made of the elastically resilient metal and a strip made of the metal with the high conductivity flat on top of one another and connecting them integrally. The integral connection is usually brought about by cold welding under pressure, more particularly by rolling. The limbs of the forceps are made by deformation from the bimetal strip produced thus. To this end, the limbs of the forceps are stamped out of the bimetal strip, preferably available in the form of a large-area metal strip, and deformed under pressure. This affords the possibility of producing the blanks of the limbs of the forceps from the bimetal strip in a single work step by stamping and compression processing by means of a press.

The first layer made of the elastically resilient metal in the process forms the outer side of the limbs, while the second layer made of the metal with the high electrical and thermal conductivity forms the inner sides of the limbs facing one another. Here, the first layer provides the limbs of the forceps with the mechanical rigidity and the resilient properties for opening and closing the forceps. The electrodes are formed at the distal end of the limbs from the metal of the second layer. As a result of its areal extent, the second layer has a high heat capacity, with the high thermal conductivity ensuring rapid dissipation of the heat from the electrodes into the volume of the second layer.

The first layer, which forms the outer side of the limbs of the forceps, preferably consists of stainless steel. Silver or a silver alloy is preferably selected as biocompatible metal with high thermal and electrical conductivity for the second layer.

The second layer should preferably at least extend over half the length of the limb at the distal end of the limb in order to provide a sufficient volume of this layer and hence sufficient heat capacity for absorbing the dissipated heat. However, the second layer preferably extends over the entire inner surface of the limbs. A first advantage of this is the particularly high thermal capacity, and it also simplifies the production in particular because the blanks of the limbs can be stamped out of a bimetal strip with two layers throughout.

BRIEF DESCRIPTION OF THE DRAWINGS

In the following text, the invention will be explained in more detail on the basis of an exemplary embodiment illustrated in the drawing, in which:

FIG. 1 shows a bimetal strip as basic material for producing the limbs of a bipolar forceps, FIG. 2 shows a section through the bimetal strip, FIG. 3 shows a blank of a limb of the forceps formed from the bimetal strip, in a view from the outer side and from the inner side, FIG. 4 shows a side view of the limb, FIG. 5 shows an enlarged view of the distal end of the limb.

Figure 6:
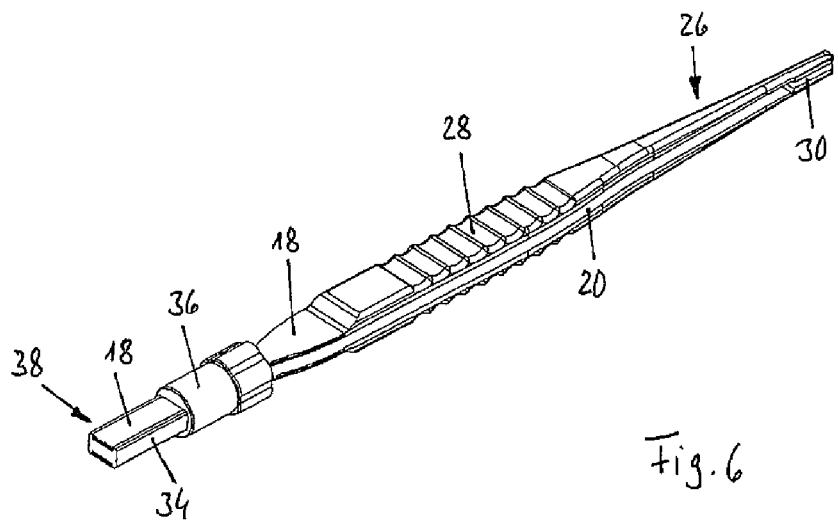
FIG. 6 shows a perspective view of the bipolar forceps and FIG. 7 shows a side view of this forceps.

In the drawing, a bipolar forceps for RF coagulation is, as an example, illustrated in an embodiment with straight limbs. Forceps with other limb shapes, e.g. curved limbs, are likewise conventional. Since the invention relates to the structure of the limbs of the forceps and not to the shape thereof, all shapes of forceps that have the structure explained below fall within the scope of the invention.

DETAILED DESCRIPTION OF THE INVENTION

In order to produce the forceps, a bimetal strip 10 is firstly produced as basic material. To this end, a strip 12 of a sheet made of an elastically resilient material and a strip 14 of a sheet made of a biocompatible metal with high electrical and thermal conductivity are placed flat on top of one another. The strip 12 preferably consists of stainless steel. The strip 14 preferably consists of silver or a silver alloy, more particularly of AgNiO.15. The strip 12 for example has a material thickness of 1.5 mm and the strip 14 for example has a material thickness of 1 mm. The strips 12 and 14 lying flat on top of one another are rolled onto one another under pressure, or are pressed onto one another, as a result of which a non-detachable integral connection is created in the contact zone by cold welding and the bimetal strip 10 is formed.

In a press, a blank of a limb 16 of the forceps is stamped out of the bimetal strip 10 in a single work stroke of the press and deformed under pressure. Depending on the areal dimensions of the bimetal strip 10, one or more limbs 16 can be produced in one work stroke of the press.

As shown in FIGS. 3 to 5, the limb 16 has a first layer 18, which forms the outer side of the limb 16 and is formed from the deformed strip 12 of e.g. stainless steel. The inner side of the limb 16 is formed by a second layer 20, which is formed from the strip 14 of e.g. a silver alloy. In the illustrated exemplary embodiment, the first layer 18 and the second layer 20 extend with their areas substantially parallel over the entire length and width of the limb 16.

In the longitudinal direction, the limb 16 has a proximal end region 22, a central region 24 and a distal end region 26. In the proximal end region 22, the limb 16 has a reduced width and is deformed to have a low material thickness, wherein the material thickness of the outer first layer 18 and inner second layer 20 is approximately equal. The central region 24 has a greater width, with the outer first layer 18 being formed to make a serrated recessed grip 28. The inner second layer 20 is not deformed in this region, and so the material thickness of the inner second layer 20 in conjunction with the width of the central region 24 forms a large volume with a high heat capacity.

The distal end region 26 of the limb 16 has a small width and tapers towards the distal tip of the limb. The second layer 20 is formed to be an electrode 30 in the region of the distal tip. In the region of this electrode 30, the material thickness of the second layer 20 is enlarged, and so the electrode 30 projects over the plane of the inner side of the limb 16 with a raised contact area 32. The second layer 20 ensures a good thermally conducting connection between the electrode 30 and the volume of the second layer 20 in the region of the recessed grip 28, and so rapid heat dissipation is ensured from the electrode 30 to the thermal capacity of the second layer 20 in the region of the recessed grip 28. With the exception of the raised electrode 30, the second layer 20 forms a continuous planar surface over the entire inner side of the limb 16.

Figure 7:
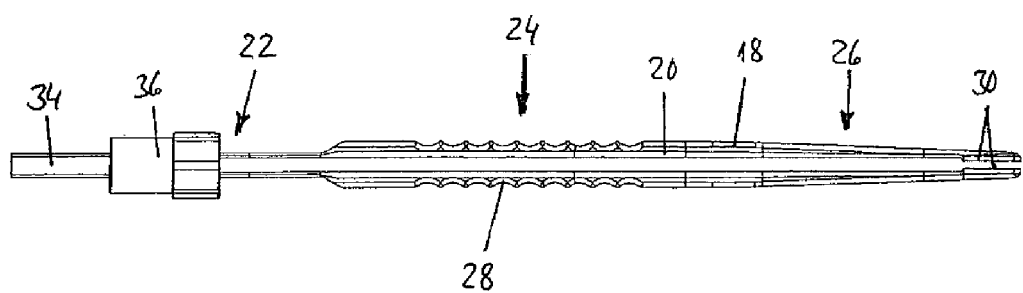

As shown by FIGS. 6 and 7, two limbs 16 are joined together in a mirror-symmetric fashion with inner sides facing one another in order to form the forceps. In the process, the proximal end regions 22 of the two limbs are encapsulated by molding by an insulating plastic material. This plastic material forms an electrical insulation 34 between the inner faces facing one another of the proximal end regions 22 of the two limbs 16. Furthermore, the plastic material forms an outer collar 36, which surrounds the proximal end regions 22 of the two limbs 16 and holds these together mechanically. The end of the limbs 16 projecting beyond the outer collar 36 in the proximal direction forms a plug 38 of a plug-in connection for an RF current supply with the first layers 18, which are respectively exposed on the outer side. On the distal side of the outer collar 36, the limbs 16 are coated by a plastic insulation that, it goes without saying, leaves at least the contact areas 32 of the electrodes 30 exposed.

During use, the forceps is connected to an RF current supply via the plug 38. For the purposes of tissue coagulation, the tissue to be coagulated is gripped with the distal tip of the forceps such that the two limbs 16 of the forceps each touch the tissue to be coagulated with the contact areas 32 of the electrodes 30. A radiofrequency current can now be conducted through the tissue via the electrodes 30, as a result of which the tissue between the electrodes 30 is heated and coagulates. Heat generated at the contact areas 32 is absorbed by the electrode 30 and very rapidly dissipated from the electrode 30 to the large volume of the second layer 20 as a result of the high thermal conductivity of the second layer 20 and the relatively large cross section thereof. As a result, it is possible to prevent the contact areas 32 from being heated and tissue from sticking onto the contact areas 32 as a result thereof.

LIST OF REFERENCE SIGNS

10 Bimetal strip
12 Stainless steel strip
14 Silver strip
16 Limb
18 First layer
20 Second layer
22 Proximal end region
24 Central region
26 Distal end region
28 Recessed grip
30 Electrode
32 Contact area
34 Insulation
36 Outer collar
38 Plug

The invention claimed is:

1. Bipolar forceps, more particularly for RF coagulation, with two limbs (16) made of an elastically resilient metal, with electrodes (30) arranged at the distal ends (26) of the limbs (16), the contact area (32) of which electrodes being formed by a biocompatible metal with high electrical and thermal conductivity, and with an electrical plug-in connector (38) arranged at the proximal end (22) of the forceps, characterized in that the limbs (16) each consist of a bimetal material at least in the distal end regions (26) thereof, which bimetal material further constitutes, on the outer sides of the limbs (16) facing away from one another, a first layer (18), which is formed by the elastically resilient metal, and, on the inner sides of the limbs (16) facing one another, a second layer (20), which is made of the metal with the high electrical and thermal conductivity, and in that the electrodes (30) are each formed from the second layer (20).

2. Forceps according to claim 1, characterized in that the first layer (18) consists of stainless steel.

3. Forceps according to claim 1, characterized in that the second layer (20) consists of silver or a silver alloy.

4. Forceps according to claim 2, characterized in that the second layer (20) consists of silver or a silver alloy.

5. Forceps according to claim 3 or 4, characterized in that the second layer (20) consists of AgNiO.15.

6. Forceps according to claim 1, 2 or 3, characterized in that the first layer (18) and the second layer (20) are interconnected by rolling or pressing.

7. Forceps according to claim 1, 2 or 3, characterized in that the second layer (20) at least extends over the distal half of the longitudinal extent of the limbs (16).

8. Forceps according to claim 1, 2 or 3, characterized in that the second layer (20) extends over the entire surface of the inner side of the limbs (16).

9. Forceps according to claim 1, 2 or 3, characterized in that the limbs have an insulating coating, which leaves at least the contact area (32) of the electrodes (30) exposed.

10. Forceps according to claim 1, characterized in that a major portion of the distal end regions (26) of the limbs (16) are constructed of the bimetal material in which the first layer (18) forms the outer sides of the limbs (16) and the second layer (20) forms the inner sides of the limbs (16).

* * * * *